United States Patent [19]

Ghosh et al.

[11] 4,362,733
[45] * Dec. 7, 1982

[54] N-CYCLOPROPYLMETHYL-14-ETHOXYMORPHINAN-6-ONE COMPOUNDS EXHIBITING MIXED ANALGESIC/NARCOTIC ANTAGONIST ACTIVITY AND PRECURSORS THEREFORE

[75] Inventors: Anil C. Ghosh, Lexington; Raj K. Razdan, Belmont, both of Mass.

[73] Assignee: Miles Laboratories, Inc., Elkhart, Ind.

[ * ] Notice: The portion of the term of this patent subsequent to Jun. 9, 1998, has been disclaimed.

[21] Appl. No.: 278,759

[22] Filed: Jun. 29, 1981

[51] Int. Cl.$^3$ .................. A61K 31/485; C07D 221/28
[52] U.S. Cl. ......................................... 424/260; 546/74
[58] Field of Search .......................... 546/74; 424/260

[56] References Cited

U.S. PATENT DOCUMENTS 3,654,280  4/1972  Sawa et al. ............................. 546/74
4,272,540  6/1981  Razdan et al. ...................... 424/260

Primary Examiner—Donald G. Daus
Assistant Examiner—Diana G. Rivers
Attorney, Agent, or Firm—Jerome L. Jeffers

[57] ABSTRACT

Disclosed are certain 14-ethoxymorphinan-6-one compounds exhibiting analgesic and, in some cases, mixed analgesic/narcotic antagonist activity.

10 Claims, No Drawings

N-CYCLOPROPYLMETHYL-14-ETHOXYMORPHINAN-6-ONE COMPOUNDS EXHIBITING MIXED ANALGESIC/NARCOTIC ANTAGONIST ACTIVITY AND PRECURSORS THEREFORE

BACKGROUND OF THE INVENTION

1. Field of the Invention

Morphine is a well known narcotic analgesic having the structural formula:

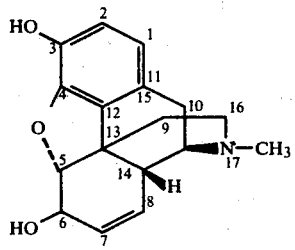

The compounds of this invention are structurally related to morphine and are named according to the morphinan system of nomenclature using the morphinan nucleus which is shown below;

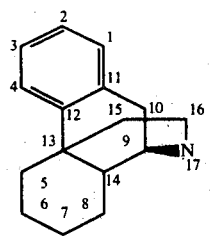

The numbering and stereochemical placement of atoms in the morphinan system is the same as that depicted for morphine. A dashed line is used to represent a covalent bond projecting below the plane of a reference atom while a wedged or heavily accented line signifies a covalent bond above such plane. The compounds of this invention have the same stereochemical placement of atoms as depicted for morphine unless otherwise indicated.

Morphine and its structurally related relatives are used primarily as analgesics. While extremely effective for the relief of moderate to severe pain these compounds are narcotic and most possess dependence-inducing ability and produce other side effects such as emesis, constipation, sweating, respiratory depression and myosis which make them less than ideal analgesics. It is impossible to predict, based on structure alone, whether a particular morphine-like compound will act as an analgesic (agonist), a narcotic antagonist or possess a combination of these properties since very minute structural modifications in the molecule can significantly change the way it affects an individual to which it is administered. A compound with the appropriate profile of analgesic (agonist) and narcotic antagonist actions has potential for treatment of moderate to severe pain without the liability of drug dependence or drug abuse. Those compounds which exhibit only agonist activity are, of course, useful as analgesics and in the case of the N-methyl compounds of the present invention, they are useful as precursors for desired mixed analgesics/narcotic antagonists by replacement of the N-methyl group with an N-cyclopropylmethyl group.

2. Prior Art

Morphinans which are hydroxy substituted in the 14-position are known. Thus, I. J. Pachter reports in *Narcotic Antagonists, Advances in Biochemical Psychopharmacology*, Vol. 8, Raven Press, New York 1973, p. 57, the preparation of compounds having the structure:

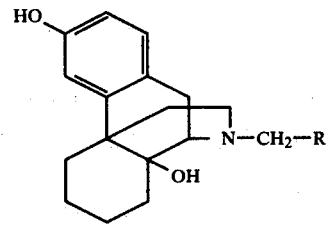

where R is cyclopropyl (A) or cyclobutyl (B). The compound in which R is cyclopropyl is reported to be essentially a narcotic antagonist while that compound in which R is cyclobutyl is reported to possess both analgesic and narcotic antagonist activity. This article also reports the preparation by the Shionogi Company in Japan of a compound having the formula:

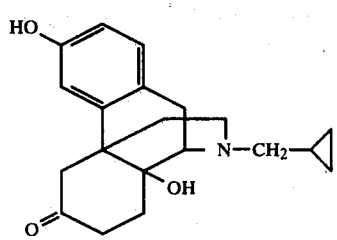

It is stated that this compound is very long-acting and more potent than (A) (above), cyclazocine or naloxone. Naloxone is a potent narcotic antagonist whereas cyclazocine has mixed analgesic/narcotic antagonist activity.

Compounds of the general formula:

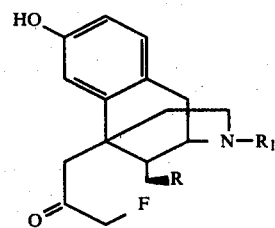

where R is a hydrogen atom or hydroxyl group; $R_1$ is allyl, $\gamma,\gamma$-dimethylallyl or cyclopropylmethyl; and F represents the presence of absence of a double bond are disclosed in U.S. Pat. No. 3,654,280 which issued Apr. 4, 1972.

SUMMARY OF THE INVENTION

The present invention involves 14-ethoxy substituted-3-hydroxy or 3-methoxy-6-one morphinans characterized by the formula:

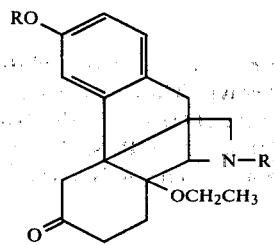

In the above formula, R is H or methyl and $R_1$ is methyl or cyclopropylmethyl.

DETAILED DESCRIPTION

The 14-ethoxymorphinan compounds of the present invention are prepared by the process set out in Scheme I:

SCHEME I

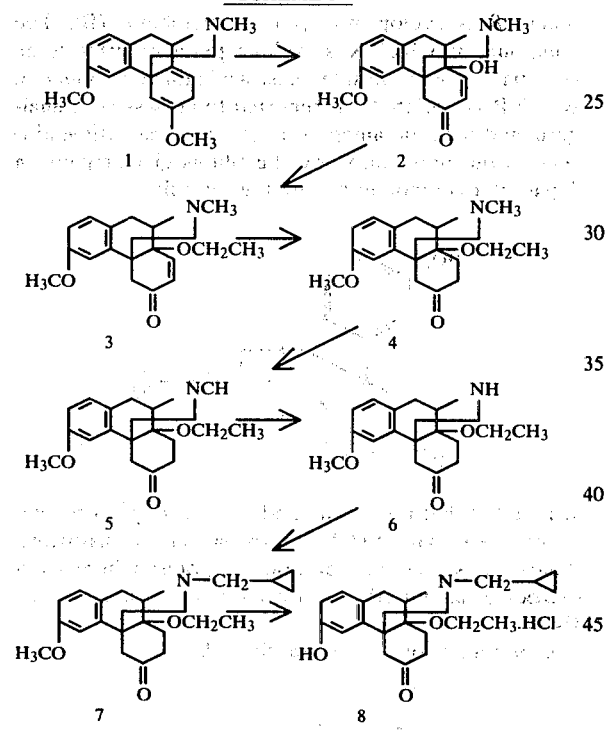

The 14-ethoxy substituted 3-hydroxy or 3-methoxy-6-one morphinans of the present invention are prepared as indicated by Scheme I. Referring to Scheme I, Compound 1 [Sawa et al, *Tetrahedron Letters*, 15, 154 (1961)] is treated with m-chloroperbenzoic acid in acid solution to give Compound 2 which is then reacted with ethyl iodide and sodium hydride to give the 14-ethoxy Compound 3. Compound 4 is obtained when 3 is hydrogenated in the presence of a catalyst such as 10% palladium on charcoal. Treatment of 4 with cyanogen bromide, followed by acid hydrolysis gives the nor Compound 6 which is reacted with an appropriate alkyl halide such as cyclopropylmethyl bromide to give Compound 7. The reaction is carried out according to standard laboratory procedures in a suitable inert solvent and in the presence of a base. Dimethylformamide and sodium bicarbonate have been used in the practice of this invention. Boron tribromide is used to selectively demethylate the methoxy in the 3-position while leaving the 14-methoxy unaffected, thus forming Compound 8. This reaction is carried out in an inert solvent and preferably under a dry atmosphere.

The preparation and pharmacology of the compounds of the present invention are more fully described in the following examples in which the compounds are numbered so as to correspond with their respective structural formulae in Scheme I.

EXAMPLE I 7,8-Didehydro-14-hydroxy-3-methoxy-17-methylmorphinan-6-one (2)

To a stirring solution of 25 g. (0.094 mole) of 3,6-dimethoxy-17-methyl-5,6,8,14-tetrahydromorphinan (1) prepared as described by Sawa et al in *Tetrahedron Letters* 15, 154 (1961) in 150 ml. of glacial acetic acid, 15 ml. of water and trifluoroacetic acid (15.04 g., 0.132 mole) held under a nitrogen atmosphere, was added m-chloroperbenzoic acid (12 g., 0.07 mole) in small portions over a 12 minute period. The reaction flask was lowered into an oil bath preheated to 95° C. and stirred for 15 minutes whereupon the flask was removed from the bath, and while stirring, additional m-chloroperbenzoic acid (7.46 g., 0.04 mole) was added over a 15 minute period. At this point the reaction mixture was again heated in the bath for 20 minutes whereupon the flask was removed from the bath, the solution stirred for an additional 30 minutes and poured into ice water. After stirring for 30 minutes the solid was removed by suction filtration, and to the chilled filtrate was added enough ammonium hydroxide to make the solution basic and precipitate a solid. After 1 hour the solid was collected by suction filtration to give 18.3 g. of crude product. Purification by chromatography on Florisil using a gradient methanol/chloroform solvent system yielded 10.0 g. (36% theory) of the desired product as a colorless solid (m.p. 213°-215° C.).

Analysis: NMR (CDCl$_3$) δ 2.43 (s, 3H, N-CH$_3$) 3.78 (s, 3H, C$_3$-OCH$_3$), 6.63-7.1 (m, 3H, aromatics). IR (neat) $\nu_{max}$ 1680 cm$^{-1}$ (>C=O).

EXAMPLE II 7,8-Didehydro-3,14-dimethoxy-17-methylmorphinan-6-one (3)

Sodium hydride (0.075 mol, 3.2 g. of a 57% dispersion in mineral oil, washed under nitrogen three times with hexane to remove the oil) was suspended in 70 ml. of dry tetrahydrofuran (distilled from sodium) and a solution of 2 (10.0 g., 0.0334 mol) in 450 ml. of dry tetrahydrofuran was added. The mixture was stirred at room temperature for 90 minutes whereupon methyl iodide (7.02 g., 0.05 mol) was added and the reaction mixture stirred at 45°-55° for four hours and then left at ambient temperature overnight. At this point the reaction was quenched by the addition of water, the layers separated and the aqueous phase extracted four times with diethyl ether. The ether extracts were combined, washed once with water and once with saturated sodium chloride, dried over sodium sulfate and concentrated under reduced pressure. The crude orange product (7.0 g.) was purified by chromatography of Florisil (graded methanol/chloroform solvent system) to yield 5.45 g. (70% theory) of the desired product.

Analysis: NMR (CDCl$_3$) δ 2.43 (s, 3H, N-CH$_3$), 3.35 (s, 3H, C$_{14}$-OCH$_3$), 3.68 (s, 3H, C$_3$-OCH$_3$), 5.81 (d, 1H, C$_7$-H).

EXAMPLE III

Preparation of
14-ethoxy-3-methoxy-17-methylmorphinan-6-one
(TR-5432) (4)

A. A dispersion of sodium hydride in mineral oil (57%, 4.22 g., 0.10 mol) was placed in a 1 liter, three-necked flask fitted with a dropping funnel, condenser and magnetic stirrer under a nitrogen atmosphere. The mineral oil was removed by washing three times with n-hexane and then 25 ml. of dry dimethylformamide (DMF) was added to the flask. A solution of 7,8-didehydro-14-hydroxy-3-methoxy-17-methylmorphinan-6-one (3) (10.0 g., 0.33 mol) in DMF (400 ml.) was added dropwise and the resulting mixture was stirred at room temperature for 45 minutes. Ethyl iodide (10.4 g., 0.67 mol) in DMF (50 ml.) was added and the resulting brownish mixture was stirred at room temperature for 1 hour. The DMF was removed under reduced pressure and the crude product was taken up in a 50:50 mixture of $CH_2Cl_2/H_2O$. The two layers were separated and the $H_2O$ layer was extracted with $CH_2Cl_2$ ($3 \times 100$ ml.). The organic extracts were combined and washed with $H_2O$ (50 ml.) dried over $Na_2SO_4$, filtered and evaporated under reduced pressure to give 8.7 g. of product as a brown oil. The crude product was chromatographed over Florisil using a graded $CHCl_3/MeOH$ solvent system to give 7.8 g. of product as a yellow solid. Recrystallization from ethanol gave 7.3 g. (68%) of purified product as colorless plates, m.p. 155°–156° C.

NMR ($CDCl_3$) δ 1.18 (t, 3H, $OCH_2CH_3$), 2.42 (s, 3H, N-CH_3), 3.72 (s, 3H, $C_3OHC_3$), 5.78 (d, 1H, $C_7$-H), 6.92 (d, 1H, $C_8$-H) and 6.55–6.88 (m, 3H, aromatics). IR ($CDCl_3$) ν max 1680 cm$^{-1}$.

Anal. Calcd. for $C_{20}H_{25}NO_3$: C, 73.35; H, 7.71; N, 4.28. Found: C, 73.29; H, 7.82; N, 4.25.

B. A solution of the material prepared in step A (7.13 g., 0.022 mol) in methanol (80 ml.) was hydrogenated over 0.7 g. of Pd/C (10%) at 3 atmospheres until the hydrogen uptake was complete. The mixture was filtered through Celite whereupon the solution was concentrated under reduced pressure to give a yellow solid. Recrystallization from ethanol afforded 5.82 g. (93%) of the title compound as peach colored needles, m.p. 171°–173° C.

NMR ($CDCl_3$) δ 1.3 (m, 3H, $OCH_2CH_3$), 2.0 (s, 3H, N-CH_3), 3.68 (s, 3H, $C_3OCH_3$) and 6.47–6.97 (m, 3H, aromatics). IR ($CHCl_3$) ν max 1700 cm$^{-1}$.

Anal. Calcd. for $C_{20}H_{27}NO_3$: C, 72.90; H, 8.28; N, 4.25. Found: C, 72.89; H, 8.32; N, 4.18.

EXAMPLE IV

Preparation of
17-cyclopropylmethyl-14-ethoxy-3-methoxymorphinan-6-one hydrochloride (TR-5440) (7)

A. Cyanogen bromide (6.98 g., 66.4 mol) and potassium carbonate (9.17 g., 66.4 mmol) were added to a solution of 3.65 g. (11.1 mmol) of 14-ethoxy-3-methoxy-17-methylmorphinan-6-one (4) prepared in Example I in $CH_2Cl_2$ (50 ml.). The mixture was refluxed for 22 hrs. and then filtered through Celite. The filtrate was washed with $H_2O$ ($2 \times 25$ ml.), dried over $Na_2SO_4$, filtered and evaporated under reduced pressure to give 3.62 g. of 17-cyano-14-ethoxy-3-methoxymorphinan-6-one as a yellow solid. This material was used without further purification.

NMR ($CDCl_3$) δ 1.4 (t, 3H, $OCH_2CH_3$), 3.8 (s, 3H, $C_3OCH_3$) and 6.67–7.17 (m, 3H, aromatics). IR ($CHCl_3$) ν max 1720 cm$^{-1}$.

B. To 3.0 g. of 17-cyano-14-ethoxy-3-methoxymorphinan-6-one (5) prepared in step A was added 50 ml. of 2 N HCl. The mixture was refluxed for 5 hours. The solution was then filtered to remove extraneous solid material and the filtrate washed with $CHCl_3$ ($2 \times 25$ ml.), made basic with 5% $NaHCO_3$ solution and extracted with $CH_2Cl_2$ ($2 \times 25$ ml.). The organic extracts were combined, dried over $Na_2SO_4$, filtered and concentrated to give 2.48 g. (89%) of 14-ethoxy-3-methoxymorphinan-6-one (6) which was used without further purification.

NMR ($CDCl_3$) δ 1.33 (t, 3H, $OCH_2CH_3$), 3.73 (s, 3H, $C_3$-$OCH_3$) and 6.6–7.10 (m, 3H, aromatics). IR ($CHCl_3$) ν max 1710 cm$^{-1}$.

C. A mixture of 14-ethoxy-3-methoxymorphinan-6-one (6) prepared in step B (1.24 g., 3.93 mmol), cyclopropylmethyl bromide (795 mg., 5.90 mmol) and $NaHCO_3$ (1.98 g., 23.6 mmol) in DMF (50 ml.) was heated under a nitrogen atmosphere for 16 hours at 110° C. The mixture was filtered and the DMF removed by distillation under reduced pressure. The residue was taken up in $CH_2Cl_2$ (150 ml.) and $H_2O$ (150 ml.) and the two layers separated. The aqueous layer was re-extracted with $CH_2Cl_2$ ($2 \times 100$ ml.) and the organic layers were combined, washed with $H_2O$ (100 ml.), dried over $Na_2SO_4$, filtered and concentrated under reduced pressure. The resulting oil was chromatographed on Florisil using graded $CH_3OH/CHCl_3$ as the eluant to give 1.241 (85%) of 17-cyclopropylmethyl-14-ethoxy-3-methoxymorphinan-6-one (7) as a yellow solid. After recrystallization from ethanol, 978 mg. (67%) of the purified product was obtained, m.p. 134°–135° C. A portion of the recovered product was converted to its HCl salt by treatment with 2 N ethereal HCl (colorless solid, m.p. 263°–265° C.).

NMR ($CDCl_3$) δ 1.3 (t, 3H, $OCH_2CH_3$), 3.73 (s, 3H, $C_3$-$OCH_3$) and 6.53–7.02 (m, 3H, aromatics). IR ($CHCl_3$) ν max 1700 cm$^{-1}$.

Anal. Calcd. for $C_{23}H_{31}NO_3$: C, 74.75; H, 8.47; N, 3.79. Found: C, 74.68; H, 8.43; N, 3.67.

EXAMPLE V

Preparation of
17-cyclopropylmethyl-14-ethoxy-3-hydroxymorphinan-6-one hydrochloride (TR-5567) (8)

The free base 200 mg. (0.54 mmol) of TR-5440 (17-cyclopropylmethyl-14-ethoxy-3-methoxymorphinan-6-one) was dissolved in 10 ml. of $CHCl_3$ and added to a stirred solution of 811 mg. (3.24 mmol) of boron tribromide in 40 ml. of $CHCl_3$ under a nitrogen atmosphere at a temperature in the range of 25°–27° C. After stirring for 25 minutes, the solution was added to a mixture of 20 g. ice/25 ml. ammonium chloride (30% solution) and stirred for an additional 16 hours whereupon the aqueous layer was separated and washed with $CHCl_3$. The organic layers were combined, dried over $Na_2SO_4$, filtered and evaporated to give an oil which was purified by column chromatography using Florisil and a graded methanol/chloroform solvent system.

NMR ($CDCl_3$) δ 1.3 (t, 3H, $OCH_2CH_3$), 5.6 (broad, 1H, OH) and 6.5–7.0 (m, 3H, aromatics), IR ($CHCl_3$) ν max 1700 cm$^{-1}$.

The free base was converted to the hydrochloride salt by treatment with ethereal HCl to give 98 mg.

(49%) of the title compound as a cream solid, m.p. >275° C.

Anal. Calcd. for $C_{22}H_{30}NO_3Cl \cdot CH_3OH$: C, 65.15; H, 8.08; N, 3.30; Cl, 8.36. Found: C, 65.43; H, 7.63; N, 3.33; Cl, 8.34.

The preparation of 17-cyclopropylmethyl-14-ethoxy-3-hydroxymorphinan-6-one can also be achieved by converting the methyl group of 17-methyl-14-ethoxy-3-hydroxy-morphinan to cyclopropylmethyl.

The analgesic and narcotic antagonist activity of the compounds prepared in the examples was determined in the following manner:

PHARMACOLOGICAL EVALUATION

The compounds whose preparation is disclosed in the foregoing examples were screened to determine the following biological activities:

(A) Analgesic effects upon mice (acetic acid writhing test).

(B) Narcotic antagonist activity in rats (modified rat tail flick test).

TEST A. ACETIC ACID MOUSE WRITHING TEST

The analgesic effects of test compounds were determined in mice by use of the acetic acid writhing test described by B. A. Whittle, *Brit.J.Pharmacol.*, 22: 246 (1964). In this test at least three groups of five male CD-1 mice each were given subcutaneous doses of the test drug dissolved in either distilled water or distilled water acidified with HCl depending on the solubility of the compound. Fifteen (15) minutes post drug, 0.4 ml. of a 0.75% or 1.0% or 0.6 ml. of a 1.0% v/v acetic acid in distilled water solution was administered intraperitoneally. The number of writhes in a 20 minute interval beginning 5 minutes after the acetic acid injection were determined and compared with the number of writhes in control groups which had received only acetic acid.

Percent inhibition of writhing was calculated as:

$$\% \text{ inhibition} = \frac{\text{No. control writhes} - \text{No. treated writhes}}{\text{No. control writhes}} \times 100$$

The $ED_{50}$ dose, i.e., the dose required to reduce the number of writhes by 50%, was determined graphically from a plot of % inhibition as a probit versus log dose. Confidence limits of 95% were calculated on the basis of those results falling in the range 16–84% inhibition. See Litchfield, J. T., and Wilcoxon, F., *J.Pharmacol.Exp.Ther.*, 96;99, (1949).

TEST B. EVALUATION OF NARCOTIC ANTAGONIST

The narcotic antagonist effects of test compounds were determined by a modification of the rat tail flick procedure of Harris and Pierson, *J.Pharmacol.Exp.Ther.* 143:141 (1964).

Male albino Wistar rats (100–120 g.) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from 1.7 to 5.6 seconds. Animals with a control reaction time outside this range are rejected. The rheostat adjustment is made only if a significant proportion (more than 1 out of every 10 rats) of the reaction times are outside the range of 2 to 4 seconds. Groups of five rats were used each time, and two control times were determined at least 30 minuts apart.

The test drug was given intraperitoneally and this was followed ten minutes later by an $ED_{80}$ dose of morphine subcutaneously. The animals were retested at 20 minutes after the morphine injection. Control animals were given morphine only. A ten second cutoff time is employed; if the rat does not flick its tail in 10 seconds it is removed from the heat source. The data was calculated as follows:

$$\% \text{ Effect } (E) = \frac{MRT^* \text{ (Treated)} - MRT \text{ (Control)}}{10 - MRT \text{ (Control)}} \times 100$$

$$\% \text{ Antagonism} = \frac{E \text{ (morphine controls)} - E \text{ (drug treated)}}{E \text{ (morphine control)}} \times 100$$

*$MRT$ is defined as Mean Reaction Time.

The date was plotted on log-probit paper and $AD_{50}$ values, i.e., the dose required to inhibit the morphine effect by 50% within 95% confidence limits, were determined by the method of Litchfield and Wilcoxon.

The foregoing tests were used to determine that the $ED_{50}/AD_{50}$ values for TR-5440 and TR-5567 were 0.53/0.175 and 1.47/0.25, respectively, and that the $ED_{50}$ for TR-5432 was 0.50 mg./kg. From the foregoing data, it can be determined that TR-5432 is a powerful analgesic whereas compounds TR-5440 and TR-5567 possess mixed analgesic/narcotic antagonist activity. These compounds are of special interest because they are useful for treating moderate to severe pain in an individual without the liability of drug dependence.

The term "individual" means a human being or an experimental animal that is a model for a human being. The dose to be administered to achieve the desired result, i.e., the effective dose, may vary from individual to individual but is readily determined by one skilled in the art without undue experimentation.

The compounds of the present invention form pharmacologically active addition salts with organic and inorganic acids. Acid addition salts are normally preferred due to their increased water solubility and the resulting greater ease of administration. These compounds may be administered by known, conventional methods of therapeutic administration such as intravenous, parenteral, buccal, rectal or oral. Dose forms for the administration of these compounds can be prepared by methods recognized in the pharmaceutical sciences.

What is claimed is:

1. 14-ethoxy substituted-3-hydroxy or 3-methoxy-6-one morphinans characterized by the formula:

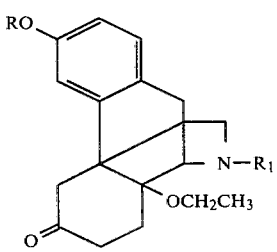

wherein R is H or methyl and $R_1$ is methyl or cyclopropylmethyl.

2. A compound as defined by claim 1 wherein R is methyl and $R_1$ is cyclopropylmethyl.

3. A compound as defined by claim 1 wherein R is H and $R_1$ is cyclopropylmethyl.

4. A compound as defined by claim 1 wherein R is methyl and $R_1$ is methyl.

5. A compound as defined by claim 1 wherein R is H and $R_1$ is methyl.

6. A compound as defined by claim 1 in the form of its pharmacologically acceptable acid addition salt.

7. A therapeutic method for treating pain in an individual for whom such therapy is indicated, which method comprises administering to the individual an effective analgesic amount of a compound characterized by the formula:

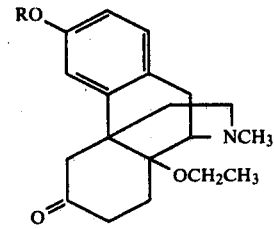

where R is H or methyl.

8. A therapeutic method for treating pain without liability of drug dependence in an individual for whom such therapy is indicated which method comprises administering to the individual an effective analgesic amount of a compound characterized by the formula:

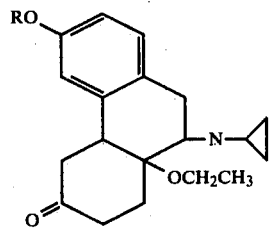

where R is H or methyl.

9. The method of claim 8 wherein R is H.

10. The method of claim 8 wherein R is methyl.

* * * * *